United States Patent
Dorronsoro Díaz et al.

(10) Patent No.: US 12,318,141 B2
(45) Date of Patent: Jun. 3, 2025

(54) APPARATUS AND SYSTEM FOR THE PERFORMANCE OF OPTOMETRIC MEASUREMENTS AND METHOD FOR ADJUSTING THE OPTICAL POWER OF AN ADJUSTABLE LENS

(71) Applicant: CONSEJO SUPERIOR DE INVESTIGACIONES CIENTÍFICAS, Madrid (ES)

(72) Inventors: Carlos Dorronsoro Díaz, Madrid (ES); Victor Rodríguez López, Madrid (ES)

(73) Assignee: CONSEJO SUPERIOR DE INVESTIGACIONES CIENTÍFICAS, Madrid (ES)

( * ) Notice: Subject to any disclaimer, the term of this patent is extended or adjusted under 35 U.S.C. 154(b) by 684 days.

(21) Appl. No.: 17/435,823

(22) PCT Filed: Mar. 4, 2020

(86) PCT No.: PCT/ES2020/070161
§ 371 (c)(1),
(2) Date: Sep. 2, 2021

(87) PCT Pub. No.: WO2020/178471
PCT Pub. Date: Sep. 10, 2020

(65) Prior Publication Data
US 2022/0151485 A1    May 19, 2022

(30) Foreign Application Priority Data
Mar. 4, 2019 (ES) .................................. 201930198

(51) Int. Cl.
*A61B 3/032* (2006.01)
*G02F 1/01* (2006.01)
*G02F 1/19* (2019.01)

(52) U.S. Cl.
CPC .......... *A61B 3/0325* (2013.01); *G02F 1/0126* (2013.01); *G02F 1/19* (2013.01)

(58) Field of Classification Search
CPC ........... A61B 3/006; A61B 3/063; A61B 3/06; A61B 3/04; A61B 3/02; A61B 3/0336; G02F 1/19; G02F 1/0126
See application file for complete search history.

(56) References Cited

U.S. PATENT DOCUMENTS 7,524,065 B1 * 4/2009 Ogilvie ................. A61B 3/032
351/222
9,572,487 B2 * 2/2017 Gaton .................... G02C 7/085
(Continued)

OTHER PUBLICATIONS

Florent Thieblemont et al., "A novel liquid lens optical component capable of focus and astigmatism correction: application to an innovative phoropter", DataBase, Jun. 2015, pp. 1-2, Iovs.
(Continued)

*Primary Examiner* — Christopher Stanford
*Assistant Examiner* — Journey F Sumlar
(74) *Attorney, Agent, or Firm* — Snell & Wilmer LLP

(57) ABSTRACT

An apparatus for performing optometric measurements includes an opto-adjustable lens, the optical power of which is adjustable, with the lens being controlled by a periodic signal configured for producing a periodic optical power wave over time. The apparatus also includes a component for the adjustment of the mean value of the periodic optical power wave. The apparatus further includes an optical projector system for projecting a plane of the opto-adjustable lens onto a plane external to the apparatus, and in that the periodic signal has an amplitude such that it produces an amplitude of the periodic optical power wave corresponding to a chromatic difference of focus between a first wavelength and a second wavelength of visible light which passes the opto-adjustable lens. A system for the performance of opto-
(Continued)

metric measurements and a method for adjusting the optical power of an adjustable lens are related to the apparatus.

18 Claims, 5 Drawing Sheets

(56) References Cited

U.S. PATENT DOCUMENTS

| | | | |
|---|---|---|---|
| 10,171,725 B1 | 1/2019 | Nahum et al. | |
| 2006/0146283 A1* | 7/2006 | Baumann | A61B 3/113 351/208 |
| 2006/0152676 A1* | 7/2006 | Baumann | A61B 3/113 351/205 |
| 2011/0066143 A1* | 3/2011 | Bischoff | G16H 10/60 606/4 |
| 2012/0019775 A1* | 1/2012 | Tyrin | A61H 5/00 351/203 |
| 2012/0287398 A1* | 11/2012 | Baker | A61B 3/103 351/201 |
| 2013/0222764 A1 | 8/2013 | Thompson et al. | |
| 2014/0362345 A1* | 12/2014 | Baranton | A61B 3/0025 351/212 |
| 2015/0185503 A1* | 7/2015 | Tate | G02C 7/083 351/159.01 |
| 2015/0216411 A1 | 8/2015 | Gaton et al. | |
| 2017/0318216 A1 | 11/2017 | Gladnick et al. | |
| 2019/0002656 A1 | 1/2019 | Liu et al. | |

OTHER PUBLICATIONS

International Search Report issued Jun. 24, 2020 re: Application No. PCT/ES2020/070161, pp. 1-4, citing: Thieblemont et al. "A novel liquid lens . . . " US 2019002656 A2, US 2015216411 A1, US2017318216 A1, US 2013222764 A1 and U.S. Pat. No. 10,171,725 B1.

* cited by examiner

APPARATUS AND SYSTEM FOR THE PERFORMANCE OF OPTOMETRIC MEASUREMENTS AND METHOD FOR ADJUSTING THE OPTICAL POWER OF AN ADJUSTABLE LENS

TECHNICAL FIELD

The present disclosure relates to the field of ophthalmology. More specifically, it relates to an apparatus, a system, and a method for determining a lens which corrects ametropia.

BACKGROUND

Ametropia is an eye defect which causes an image to be unsuitably focused on the retina, leading to reduced visual acuity. Main ametropias include myopia and hypermetropia. It is estimated that half of young adults in the United States and Europe and up to 90% of young adults in China have myopia. It has been estimated that half of the population will have myopia by 2050. Subjective refraction is a procedure for determining a lens which corrects ametropia in a patient.

Conventional subjective refraction is a routine procedure in the field of eye care that has not changed much and in fact still constitutes a tedious process for patients and ophthalmologists. In this procedure, the patient looks through different lenses, evaluating whether the perceived image is less blurry in comparison with other lenses which he or she has previously tried. The patient then informs the ophthalmologist whether the perceived image is more or less blurry and the ophthalmologist decides which lens should be tried next. This method is repeated until the ophthalmologist decides that an optimal lens has been found based on his or her interpretation of the information passed on by the patient.

Normally, this procedure can be performed using different devices such as a pair of test glasses, the lenses of which are progressively changed, or a phoropter, either a manual phoropter or the evolution thereof into a digital phoropter, in which the movement of the lenses is automated and performed in combination with a projector which is also automated. There are also phoropters with adjustable lenses.

In any of the cases, the task performed by the patient is relative to the degree of blurring with which he or she perceives an image. It is a difficult task because the patient must remember how blurry the image perceived with the preceding lenses was and compare this memory with how blurry the image perceived with the current lens is. This translates into a high level of uncertainty in the results, in addition to the generation of certain insecurity in the patient; and this leads to a time-consuming procedure that additionally requires the presence of an optometrist or ophthalmologist.

Moreover, the direction in which the lens shift must be performed in order to improve the patient's vision is not known a priori, so the procedure may take even longer from start to finish.

Furthermore, the patient may be accommodating (changing the optical power of his or her own eye) throughout the test, with this accommodation interfering in the actual test result. This is particularly important in the case of young hypermetropic patients who unconsciously compensate for their ametropia completely or partially by means of accommodation. The consequence of unconsciously focusing otherwise out-of-focus stimuli on the retina is that the resulting subjective refraction is distorted. There are several strategies for reducing the effect of accommodation on subjective refraction based on relaxing the accommodation with different types of lenses, but drops which stop the accommodation are often resorted to. Stopping the accommodation using pharmaceutical substances is uncomfortable for the patient since the drops also dilate the pupil and cause visual disturbances after visual examination, often for several hours.

In other words, regardless of which of the aforementioned devices is used in subjective refraction, the conventional method presents the following problems:
- It is a method which requires the intervention and supervision of an optometrist or ophthalmologist.
- Interference may occur as a result of accommodation, so drops to stop pupil accommodation are often required.
- It is a method that proves difficult for the subject and for the optometrist or ophthalmologist.
- It is based on the trial and error of different lenses.
- It takes time to carry out the entire procedure.
- Disparities may be produced in the responses.

Patent document US-2015/0216411-A1 presents a method and a device for interactive adjustment of a continuously variable optical lens. According to this method, a parameter of the variable optical lens is modulated around and the mean value of this parameter of the variable optical lens is adjusted to minimise the flicker perceived by the subject.

Although the method described in this patent document improves the quality of the results obtained with respect to conventional subjective refraction methods, since the visual task of assessing or detecting flicker is easier than that of assessing or detecting blurring, the method proposed in US-2015/0216411-A1 still poses many of the problems of the conventional subjective refraction procedure; particularly, this method is based on the trial and error of different conditions since the subject does not know the direction in which the parameter must be modified, and therefore it takes time to carry out the entire procedure and disparities many be produced in the responses.

There is therefore the need for a subjective refraction procedure that is simpler, more precise, and more direct for the patient and the ophthalmologist, and the results of which are minimally affected by variability in the subjective responses of the patient.

SUMMARY

To overcome the drawbacks of the state of the art, the present disclosure proposes an apparatus and a system for performing optometric measurements, as well as a method for adjusting the optical power of an opto-adjustable lens, which solve the problems posed by the existing systems, given that they allow a simpler, more precise, and more direct evaluation and the results of which are minimally affected by variability in the subjective responses of the patient.

A first aspect of the disclosure proposes an apparatus for performing optometric measurements comprising:
- an opto-adjustable lens the optical power of which is adjustable, said opto-adjustable lens being controlled by a periodic signal configured for producing a periodic optical power wave; and
- means for adjusting the mean value of the periodic optical power wave.

The apparatus further comprises an optical projector system for projecting a plane of the opto-adjustable lens onto a plane external to the apparatus. According to the disclosure, the periodic signal has an amplitude such that it produces an amplitude of the periodic optical power wave corresponding to a chromatic difference of focus between a first wavelength and a second wavelength of visible light which passes the opto-adjustable lens.

For the purposes of this disclosure, chromatic difference of focus, in reference to two wavelengths of incident light, is understood as the difference between the optical powers corresponding to said wavelengths in dioptres.

The plane external to the apparatus onto which the plane of the opto-adjustable lens is projected is fixed, i.e., it does not change when the mean value of the periodic optical power wave is adjusted.

In some embodiments, the plane external to the apparatus is a plane in which the pupil of the eye of a subject is located, and the chromatic difference of focus is that which is produced in the eye of the subject when the subject looks through the apparatus. Therefore, the apparatus allows the subjective refraction of the eye of the subject to be measured in a quick, simpler, and more precise manner in comparison with conventional subjective refraction.

According to the proposed apparatus, the optical projector system projects a plane of the opto-adjustable lens onto another plane external to the apparatus, such as the pupil of the eye of the subject, and this opto-adjustable lens is modulated according to a periodic signal which is adjusted to produce a periodic optical power wave the amplitude of which corresponds with the chromatic difference of focus between two wavelengths visible to the subject; therefore, the apparatus generates an image with fluctuating defocusing on both sides of the retina. When the subject looks through the apparatus of the disclosure, he or she perceives an image with fluctuating defocusing, but without change in magnifications as a result of the optical projector system. The proposed apparatus further comprises means for adjusting the mean value of the periodic signal to enable modifying the fluctuation and chromatic effects of the image perceived by the subject.

The periodic optical power wave can be a square wave, causing a more abrupt change and thereby emphasising the chromatic effects.

The periodic optical power wave has a frequency lower than the threshold frequency of the human visual system or flicker fusion threshold. By using a frequency that is lower than the fusion threshold frequency, the subject can perceive flicker. In some embodiments, the frequency is between 10 and 30 Hz, given that flicker is visible to the human eye in this range of frequencies and preferably when the frequency is 15 Hz. These frequencies of the periodic optical power wave are high enough so as to prevent the accommodation of the eye of the subject, i.e., focusing variations are too fast for the eye to be able to follow same, and low enough so as to be below the flicker fusion threshold frequency.

One of the at least two different colours of a visual stimulus perceived by the eye of the subject is a combination of the first wavelength and the second wavelength; in some embodiments, another one of the at least two different colours is black (absence of light).

The apparatus further comprises means for adjusting the amplitude of the periodic optical power wave to different combinations of values of the first wavelength and of the second visible wavelength.

The amplitude of the periodic optical power wave (measured from peak to valley) can be between 0.25 dioptres and 3 dioptres. Optical power amplitudes of 0.25 dioptres correspond with deviations of about 0.125 dioptres with respect to the mean value and are hard to perceive in clinical practice. Optical power amplitudes of 3 dioptres correspond with deviations of about 1.5 dioptres which are also hard to compare, in this case due to excessive blurring.

The amplitude of the periodic optical power wave (measured from peak to valley) can be in a range between 0.75 and 1.5 dioptres, corresponding with the chromatic difference of focus between a first visible red wavelength and a second visible blue wavelength. In this case, the visual stimulus shown to the subject contains elements with at least two different colours, of which one is magenta (combination of red and blue) and the other is usually black.

The amplitude of the periodic optical power wave (measured from peak to valley) can be in a range between 0.25 and 0.75 dioptres, corresponding with the chromatic difference of focus between a first visible green wavelength and a second visible red wavelength. In this case, the visual stimulus shown to the subject contains elements with at least two different colours, of which one is yellow (combination of green and red). This range of dioptres also corresponds with the chromatic difference of focus between a first visible green wavelength and a second visible blue wavelength. In this case, the visual stimulus shown to the subject contains elements with at least two different colours, of which one is bluish green (combination of green and blue). In any of these combinations, green/red or green/blue, the other colour used in the stimulus is black.

In some embodiments, the apparatus further comprises a variable iris diaphragm. This variable iris diaphragm limits the visual field and provides the visual field with a soft edge, which is not perceptually affected by the periodic optical power wave and therefore has no perceptual impact on the task.

The optical projector system keeps the magnification and position of the image perceived by the subject constant in light of different optical power values of the opto-adjustable lens.

The apparatus may further comprise securing means for being fixed to the head of the subject.

The subject may have access to the means for adjusting the mean value of the periodic optical power wave.

Another aspect of the disclosure relates to a system for performing optometric measurements on an eye of a subject. This system comprises:

a visual stimulus with elements in at least two different colours; and an apparatus for performing optometric measurements according to any of the described embodiments.

One of the at least two different colours of the visual stimulus is a combination of the first wavelength and the second wavelength which produces the chromatic difference of focus in the eye of the subject. The first and second wavelengths can be blue and red, and one of the at least two colours of the elements of the visual stimulus can be magenta. The first and second wavelengths can be green and red, or green and blue, and one of the at least two colours of the elements of the visual stimulus can be yellow or bluish green; the other one of the at least two colours of the elements of the stimulus can be black.

Another aspect of the disclosure relates to a method for adjusting the optical power of an opto-adjustable lens. The method comprises:

making a subject look at a visual stimulus through an opto-adjustable lens the optical power of which is adjustable, projecting a plane of the opto-adjustable lens onto the pupil of an eye of the subject;

controlling the opto-adjustable lens by means of a periodic signal and producing a periodic optical power wave the amplitude of which corresponds to a chromatic difference of focus produced in the eye of the subject between a first wavelength and a second wavelength of visible light, the visual stimulus comprising elements in at least two different colours, one of the at least two colours being a combination of the first wavelength and the second wavelength; and adjusting the mean value of the periodic optical power wave to eliminate chromatic effects and fluctuation of the visual stimulus perceived by the subject, or to reduce the size and intensity of said chromatic effects to the minimum.

This fluctuation is not a spatial fluctuation, since the visual stimulus is kept in the same position and with the same magnifications as a result of the optical projector system; the fluctuation is produced in blurring or defocusing, or in the size and intensity of the chromatic effects, or in all of the foregoing at the same time.

The method for adjusting the optical power of an opto-adjustable lens can be performed with the apparatus for performing optometric measurements described above, the opto-adjustable lens being the opto-adjustable lens of said apparatus.

The step of projecting a plane of the opto-adjustable lens onto the pupil of an eye of the subject can be performed by means of an optical projector system.

The method may comprise measuring the optimal spherical equivalent using a bichromatic stimulus. To that end, the defocusing wave has a variable mean value and a fixed amplitude. The method includes the step of adjusting the mean value of the periodic optical power wave until the chromatic effects perceived by the subject in the visual stimulus are eliminated or the size and intensity thereof reduced to the minimum.

A quick method for obtaining an estimate of the optimal spherical equivalent that is more precise than the conventional method, is valid in the presence of astigmatism, and does not require stopping accommodation, is therefore provided.

The chromatic effects perceived by the subject in the visual stimulus can include a colour change to blue or red, in the event that the visual stimulus includes magenta elements. If the visual stimulus includes yellow elements, the chromatic effects can include a colour change to green or red; or if the visual stimulus includes bluish green elements, the chromatic effects can include a colour change to green or blue.

The described method can be carried out with an apparatus as described above.

The apparatus, system, and method proposed in the present description have the following advantages with respect to known methods and systems:

The task of assessing blurring becomes a task of detecting fluctuation and chromatic effects in the perceived image. Therefore, it is a simpler and more intuitive task, in addition to being more precise.

By means of perceiving fluctuation and chromatic effects, an indication of the direction of the focus is obtained, so the process of examining the patient is faster.

It is not subject to accommodation since the accommodation system does not have time to follow the optical power wave. Unconscious accommodation is therefore deactivated. Furthermore, the task required of the subject is not based on image quality, and therefore the subject does not consciously make an effort to accommodate.

The procedure can be carried out with minimal (or even zero) supervision by the ophthalmologist or optometrist: the procedure and the way to use the apparatus are explained to the subject, and the subject is instructed to stop when he or she no longer sees the visual stimulus with minimal fluctuation and without chromatic effects.

The different aspects and embodiments of the disclosure defined above can be combined with one another, provided that they are mutually compatible.

Additional advantages and features of the disclosure will become apparent based on the following detailed description and will be specified particularly in the attached claims.

BRIEF DESCRIPTION OF THE DRAWINGS

To complement the description and for the purpose of helping to better understand the features of the disclosure according to several practical exemplary embodiments of the disclosure, a set of figures is attached as an integral part of the description in which the following is depicted in an illustrative and non-limiting manner.

DETAILED DESCRIPTION OF THE DRAWINGS

In the description of the possible preferred embodiments of the disclosure, various details must be provided to favour a better understanding of the disclosure. Nevertheless, it will be apparent for one skilled in the art that the disclosure can be implemented without these specific details. Moreover, well-known features have not been described in detail to prevent unnecessarily complicating the description.

Figure 1:
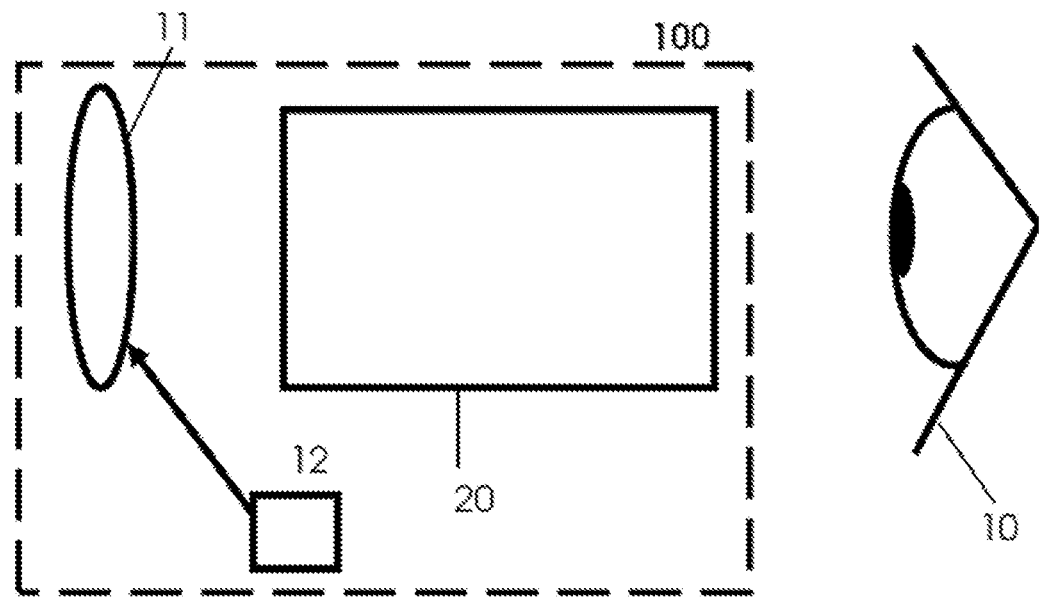
FIG. 1 is a schematic depiction of an apparatus for performing optometric measurements according to a possible embodiment of the disclosure in which the place where an eye is located in the usage position is furthermore shown.

FIG. 1 schematically shows an apparatus for performing optometric measurements according to a possible embodiment of the disclosure thereof. This schematic depiction shows the apparatus 100 for optometric measurements of a subject, as well as the place where the eye 10 of the patient is located in the usage position of the apparatus 100.

As shown in this FIG. 1, the apparatus 100 comprises an opto-adjustable lens 11 the optical power of which is adjustable, as well as an actuator 12 to enable adjusting the mean value VM of the optical power wave. The apparatus 100 also includes an optical projector system 20 projecting a plane of the opto-adjustable lens 11 onto a plane external to the apparatus at a specific distance where the pupil of the eye 10 of the patient is located.

The apparatus 100 has an optical path optically connecting the opto-adjustable lens 11 and a peephole or blinders after which the eye 10 of the patient must be positioned. As shown in FIG. 1, the optical projector system 20 is located in an intermediate position of said optical path.

At a high velocity, the opto-adjustable lens 11 is capable of changing the curvature of at least one of its faces, made of a polymer material, in response to having an electrical signal applied thereto. In any case, this opto-adjustable lens 11 is capable of spanning an optical power interval of several dioptres.

In the shown embodiment of the apparatus 100, the electrical signal applied to the opto-adjustable lens 11 is a periodic signal, such that it produces a periodic optical power wave over time. By applying this periodic signal to the opto-adjustable lens 11 and by means of the optical projector system 20, periodic variations in the blurring of the image are produced on the retina of the patient.

In the shown embodiment, the apparatus 100 includes a single casing (schematically depicted by the dashed line) containing therein the opto-adjustable lens 11 and the optical projector system 20. In fact, the apparatus 100 can be implemented in a device with Sim+Vis Technology®, marketed by 2EyesVision. There is therefore provided a compact, all-in-one, and inexpensive phoropter (which can weigh about 1 kg), with advantages over the known methods and systems described above.

Figure 2:
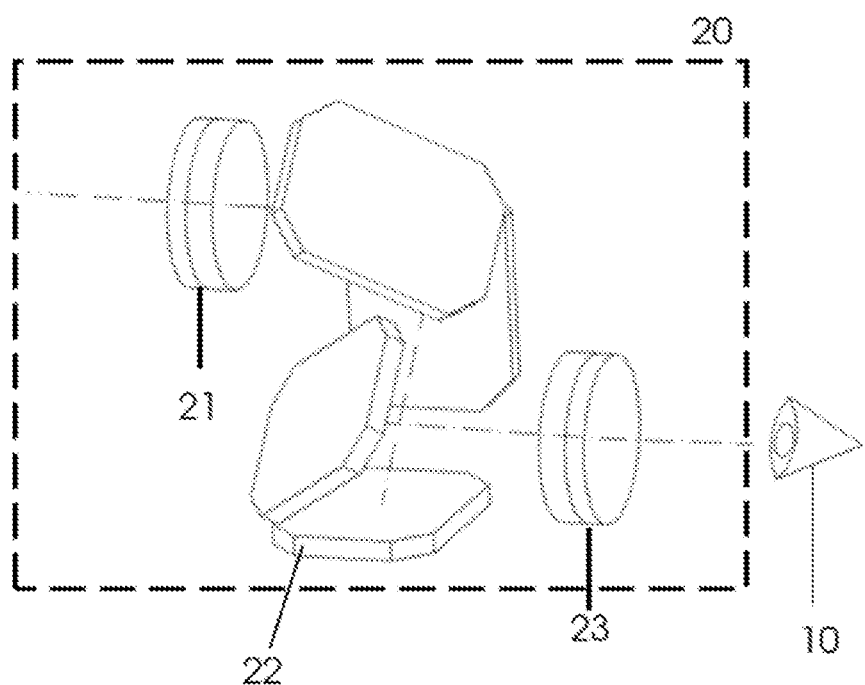
FIG. 2 shows a particular embodiment of the optical projector system.

FIG. 2 shows a particular embodiment of the optical projector system 20. The projector system 20 comprises a first lens 21, a mirror inverter group 22 that vertically and horizontally inverts the image, and a second lens 23. The first lens 21 and the second lens 23 have a configuration similar to a Badal system. The first lens 21 is positioned at one focal distance from the opto-adjustable lens 11 and the second lens 23, which is identical to the first lens 21, is positioned at two focal distances from the first lens 21. The pupil of the eye 10 is positioned at one focal distance from the second lens 23. These distances refer to measurements along the optical axis.

As a result, when the optical power of the opto-adjustable lens changes, the optical projector system provides images in the eye of the patient always in the same position and with the same magnifications, although the degree of focusing thereof, and therefore the blurring thereof, changes.

The mirror inverter group 22 is similar to a pair of Porro prisms used in prismatic telescopes for earth observation that is, however, implemented with mirrors; this inverter group compensates for image inversion, inverting it vertically and horizontally.

As explained above, the opto-adjustable lens 11 is controlled by a periodic signal with a frequency of 15 Hz which produces a periodic optical power wave over time which in turn causes periodic variations in the blurring of the image produced on the retina of the patient. In other words, this periodic optical power wave can be considered a periodic defocusing wave.

Though not shown in FIG. 2, a variable iris diaphragm with a maximum aperture of 9 mm can be placed at the end of the assembly (out of focus); this variable iris diaphragm acts as a field diaphragm. Objects located on the periphery of the visual field can thereby be concealed. Stimulus limits, screen edges, the table, etc., may distract the observer, and provide, with their abrupt edges, an unwanted accommodation stimulus in these measurements. Furthermore, this variable iris diaphragm (or field diaphragm) facilitates the centring of the subject and limits the view to the centre of the visual field which is the area of the optical system with the best optical quality. Since it is out-of-focus, the field diaphragm has extremely blurry edges. The field edges thus introduced are much softer than the content of the stimuli and are not affected by the defocusing wave, i.e., they have no perceptual impact on the task.

Figure 3:
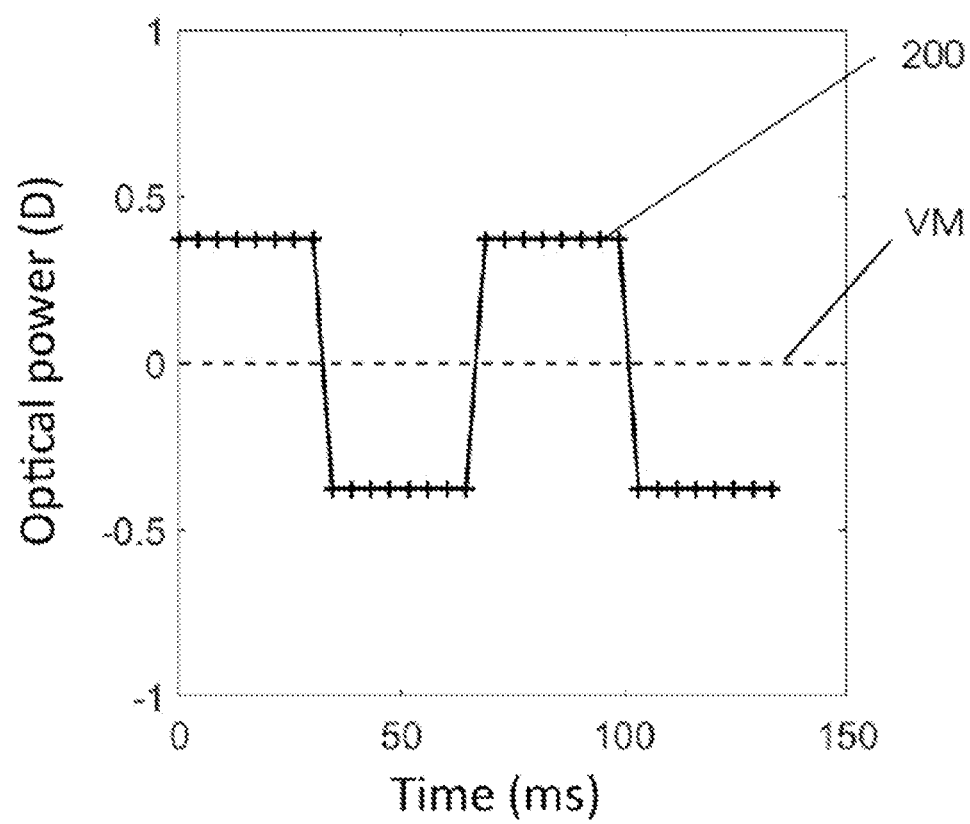
FIG. 3 shows an example of an optical power wave the frequency of which is 15 Hz.

FIG. 3 shows an example of this defocusing optical power wave 200 the frequency of which is 15 Hz and the amplitude of which is 0.75 dioptres. In this particular example, the mean value is zero, although this is a variable parameter during the use of the apparatus.

For chromatic effects to be produced in the image perceived by the subject, the amplitude of the optical power wave 200 must correspond with the chromatic difference of focus between a first wavelength and a second wavelength of the visible light which passes the opto-adjustable lens 11. The amplitude of the optical power wave 200 shown in FIG. 3 is 0.75 dioptres, corresponding with the chromatic difference of focus in the eye of the subject between a first visible red wavelength R and a second visible blue wavelength λ. Furthermore, the difference between the first wavelength and the second wavelength of visible light which passes the opto-adjustable lens 11 must be sufficient so that the patient also perceives the chromatic effects, in addition to blurring fluctuations.

Figure 4:
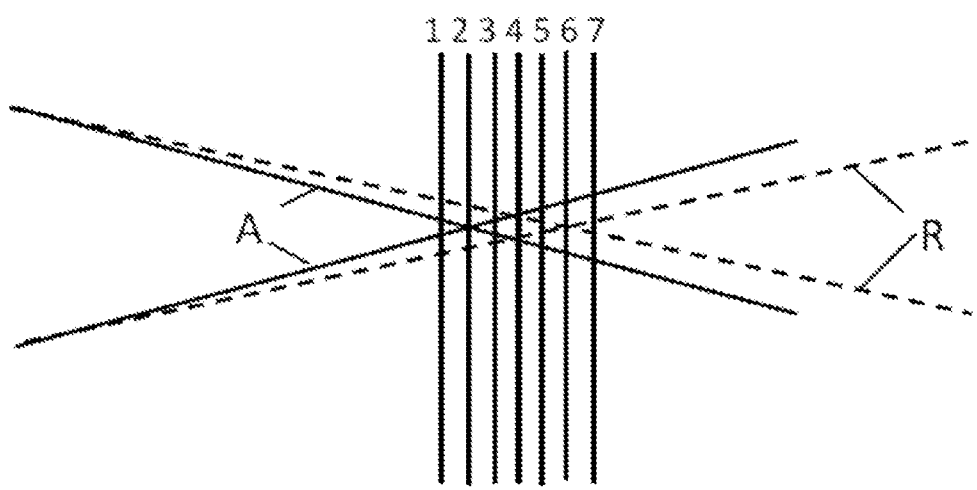
FIG. 4 illustrates the chromatic difference of focus between a first wavelength and a second wavelength, red and blue, of the visible light which passes the opto-adjustable lens.

FIG. 4 illustrates the chromatic difference of focus between the first red wavelength R and the second blue wavelength A of visible light which passes the opto-adjustable lens 11; straight lines 1 to 7 represent possible planes of the retina. This chromatic difference of focus is the difference, in terms of optical power, between the point of convergence of the first red wavelength R and the second blue wavelength A of visible light. The point of convergence of the depicted first red wavelength R is located on the vertical plane 6; the point of convergence of the depicted second wavelength A is located on the vertical plane 2. The chromatic difference of focus between these two wavelengths is the difference between the dioptres corresponding to the plane 2 and the dioptres corresponding to the plane 6. This chromatic difference of focus is due to the fact that the eye has a different refractive index for different wavelengths; and it causes chromatic effects in the image, highlighted by the apparatus object of this description, and used for guiding the subject when adjusting the mean value of the periodic optical power wave and for determining the direction in which the mean value must be adjusted so that the optical power of the opto-adjustable lens increases or decreases.

The mean value VM of the optical power wave 200 is represented by the straight line VM, and in the case that is shown it is initially centred at 0 dioptres. As explained above, the mean value VM can be adjusted using the actuator 12, this mean value VM of the optical power wave 200 being variable in this case between −1 and +1 dioptres, but it can be more. As will be explained below, the task to which the patient is subjected (either alone or with the help of the optometrist) is the task of adjusting the mean value VM of the defocusing optical power wave until blurring fluctuation of the image is no longer perceived or until this fluctuation is minimal, something which occurs when the defocusing is symmetrical on both sides of the best subjective refraction; to that end, the actuator allows the mean value VM to be adjusted in intervals of 0.25 dioptres of coarse adjustment and 0.1 dioptres of fine adjustment.

The actuator 12 adjusts the geometry of the opto-adjustable lens 11 by acting on the electrical signal, for which the apparatus has an interface. The interface can be, among others, a user interface or an interface with a computer programme.

The interface of the actuator 12 can be located in the casing or in the proximities thereof, for example, so that the patient can comfortably access same for adjusting the mean value of the optical power wave while using the apparatus 100. It can also be located a distance from the opto-adjustable lens 11 and the optical projector system 20, so that the ophthalmologist can access it and thereby comfortably adjust the mean value of the optical power wave based on the patient's perception. This actuator may have several interfaces (e.g., one remote fixed interface, two portable interfaces, one nearby fixed interface, one for each of the two eyes of a patient, etc.). Typically, this interface is a keyboard or a pushbutton box the patient has in front of him or her or holds in his or her hands.

Figure 5A:
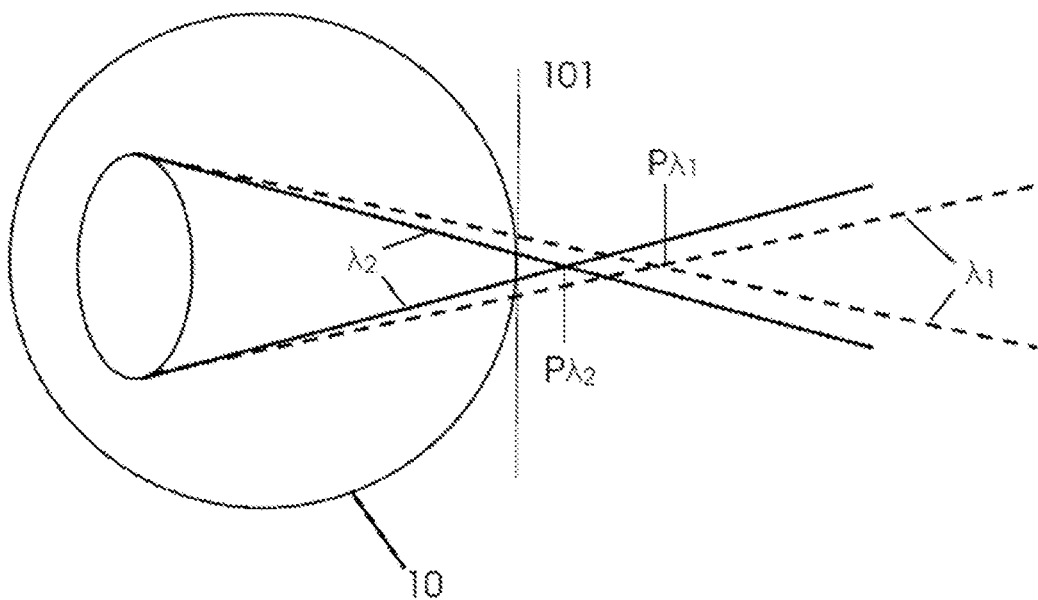
FIGS. 5A and 5B show, respectively, the effects of the two optical power waves shown in FIG. 6.
Figure 5B:
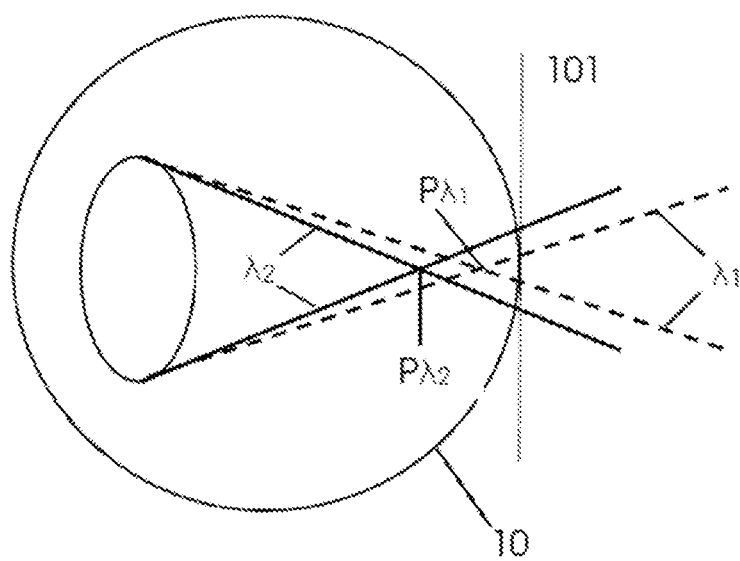
Figure 6:
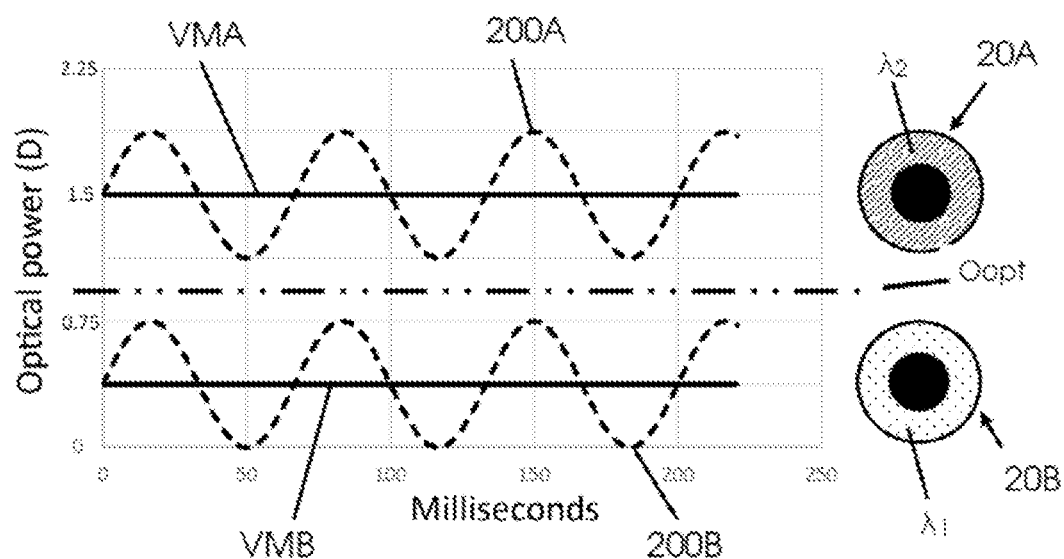

FIGS. 5A and 5B show, respectively, the effects of the optical power waves 200B and 200A of FIG. 6. The value marked as Oopt in FIG. 6 corresponds with the optimal dioptres of the lens for a supposed patient.

FIG. 5A shows that the optical power is lower than that required by the patient, since the first wavelength $\lambda_1$ and the second wavelength $\lambda_2$ converge behind the retina 101. This corresponds with the fact that the mean value VMB of the wave 200B depicted in FIG. 6 is lower than the optical power Oopt required by the patient. In the specific case in which the first wavelength $\lambda_1$ corresponds to red and the second wavelength $\lambda_2$ corresponds to blue, in the retina, a disk illuminated with the two wavelengths on a black background is perceived as a magenta disk in the central area, where both wavelengths are added up, with chromatic effects in the transition area with the background. Said chromatic effects are produced by the scattering of red light due to the greater blurring at this wavelength and comprise an inner ring and an outer ring. The outer ring with respect to the disk is dark and reddish and it is the result of the red light invading the background around the disk as it becomes blur. The inner ring with respect to the disk is bright and bluish, since the disk loses red light in that area. In contrast, for the same situation depicted in FIG. 5A, a black disk on a background illuminated with the two wavelengths will be perceived on the retina as a central black disk with a bright and bluish outer ring and a dark and reddish inner ring.

In contrast, FIG. 5B shows that the optical power is greater than that required by the subject, since the first wavelength $\lambda_1$ and the second wavelength $\lambda_2$ converge in front of the retina 101. This corresponds with the fact that the mean value VMA of the wave 200A depicted in FIG. 6 is greater than the optical power Oopt required by the patient. The chromatic effects would be opposite those of FIG. 5A.

FIG. 6 shows the chromatic effects 20A and 20B associated, respectively, with the optical power waves 200A and 200B for the case in which the stimulus is a black disk on a background illuminated with the first wavelength $\lambda_1$ which is red and the second wavelength $\lambda_2$ which is blue. The chromatic effects 20A comprise an outer ring with a higher proportion of the lower wavelength, in this case blue. The chromatic effects 20B comprise an outer ring with a higher proportion of the greater wavelength, in this case red. The chromatic effects also comprise an inner ring, not shown in the figures, in 20A with a higher proportion of the greater wavelength, in this case red, and in 20B with a higher proportion of the lower wavelength, in this case blue.

Chromatic effects appear as a result of the longitudinal chromatic aberration of the eye, but in static conditions the visual system is adapted to these effects and they are hardly perceived. However, the periodic defocusing optical power wave interacts with the chromatic effects and highlights them outside the best subjective refraction. The rings or halos change in size and intensity periodically, and therefore acquire a significant perceptual importance. Depending on many factors such as, for example, the amount of optical power, the state of adaptation of the retina to the average level of light, or the frequency of the optical power wave, some subjects will perceive only the outer ring or only the inner ring, or a certain combination of both.

For the case of FIG. 6 in which the stimulus is a black disk on a background illuminated with the first wavelength $\lambda_1$ which is red and the second wavelength $\lambda_2$ which is blue, a fluctuating outer ring which is blue appears on the myopic side and a fluctuating outer ring which is red appears on the hypermetropic side, and this provides a strong clue of the direction of the best focus.

When the mean value of the periodic defocusing optical power wave coincides with the optical power Oopt required by the patient, an exceptional circumstance arises. In that case, in the retina the chromatic effects no longer change in intensity and size. What happens is that opposite chromatic effects of the same intensity alternate between one another, losing their perceptual relevance and merging in some cases, depending on the frequency, into a neutral situation that lacks chromatic effects.

The frequency of the defocusing optical power wave 200 is lower than the flicker fusion threshold frequency so that fluctuations in the intensity and size of the chromatic effects in the myopic or hypermetropic area, where they do not change colour, are seen. Furthermore, the frequency of the defocusing optical power wave 200 is high enough so as to prevent the accommodation of the eye of the patient. Furthermore, the frequency of the defocusing optical power wave 200 favours colour fusion when the mean value of the periodic defocusing optical power wave coincides with the optical power Oopt required by the patient. The frequency of the defocusing optical power wave 200 can fall in the range of between 1 and 50 Hz, more preferably between 10 and 40 Hz; in the shown example, a frequency of 15 Hz has been used.

Figure 7:
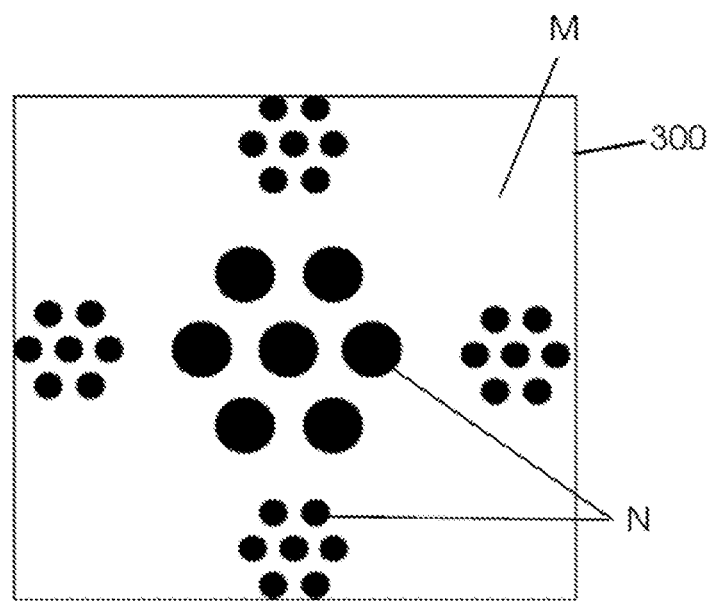
FIG. 7 shows a preferred example of an image to be used as a visual stimulus together with the apparatus of the present disclosure.

FIG. 7 shows a preferred example of a possible image to be used as a visual stimulus 300 together with the apparatus 100 of the present disclosure. The image is formed by a series of black circles N; although in FIG. 7 the background of the image is white, the background of the visual stimulus in the shown example is magenta M. The use of this visual stimulus based on clusters of black circles on a magenta (blue+red) background highlights the chromatic effects. Though not shown in FIG. 7, a contour or a line surrounding each cluster of circles could be included to further enhance the chromatic effects by causing optical watercolour illusion. The line can be a circumference, a hexagon, or an irregular line.

All tasks, i.e., reducing the intensity and size of the chromatic effects and causing the fluctuation thereof, are performed at the same time, mutually reinforcing, and intuitive for the patient, and they are not affected by a possible accommodation of the eye, which is interrupted by the defocusing wave without requiring cycloplegic drugs.

The procedure for measuring the subjective refraction of a patient includes the following steps:

i. The patient positions him or herself in front of the apparatus 100 generating this periodic defocusing wave, with a specific defocusing amplitude with respect to a mean level and a specific time frequency.

ii. The patient observes the visual stimulus with various elements (such as the one shown in FIG. 7) through the apparatus, with a specific mean value VM in the periodic defocusing wave.

iii. Based on the perceived fluctuation of the chromatic effects (in terms of both size and intensity) of one or more elements of the visual stimulus and depending on the colour of the halo perceived by the patient, an indication of the direction of the focus is obtained.

iv. The mean value VM of the periodic defocusing optical power wave is readjusted based on the chromatic effect perceived by the patient.

v. Steps iii to iv are repeated until the fluctuation of the chromatic effects perceived by the patient disappears or is minimal, and at said moment the mean value VM corresponding to the defocusing wave becomes the final mean value VM.

vi. The subjective refraction is obtained from the value of the final mean value VM in the defocusing wave.

The periodic defocusing optical power wave 200 causes fluctuation of the chromatic effects in all the mean values VM with the exception of that which coincides with the subjective refraction. When the mean value VM falls on the retina and the defocusing wave causes symmetrical blurring on both sides of the retina, the fluctuation is minimal or non-existent.

Figure 8:
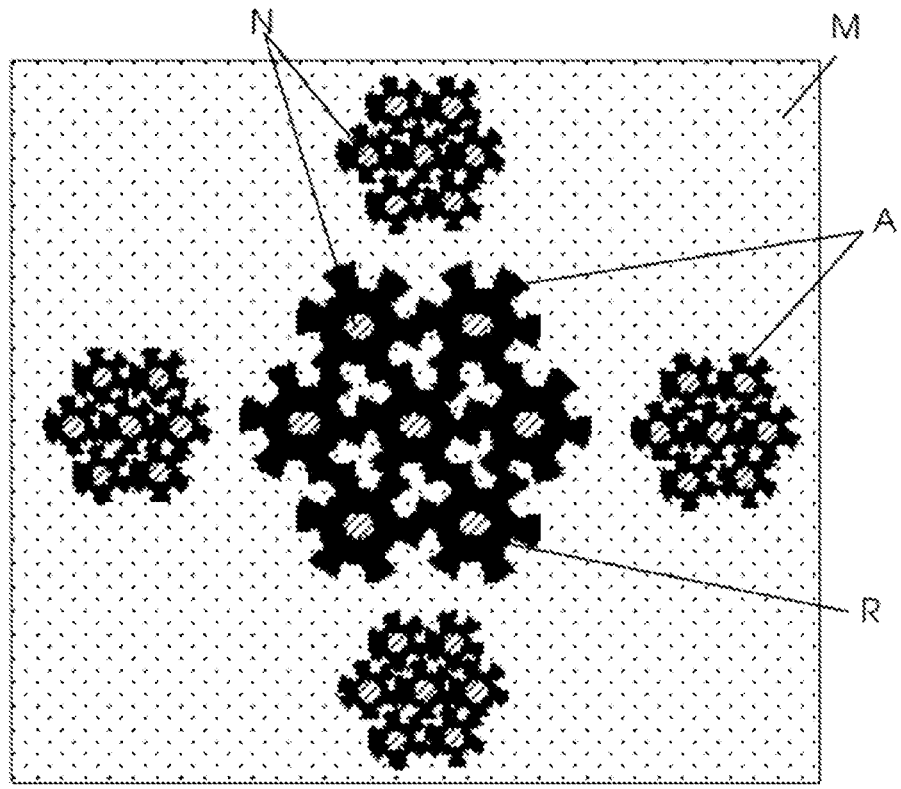
FIGS. 8 and 9 show the chromatic and flicker effects perceived by the subject during the subjective refraction procedure, using the visual stimulus of FIG. 7.
Figure 9:
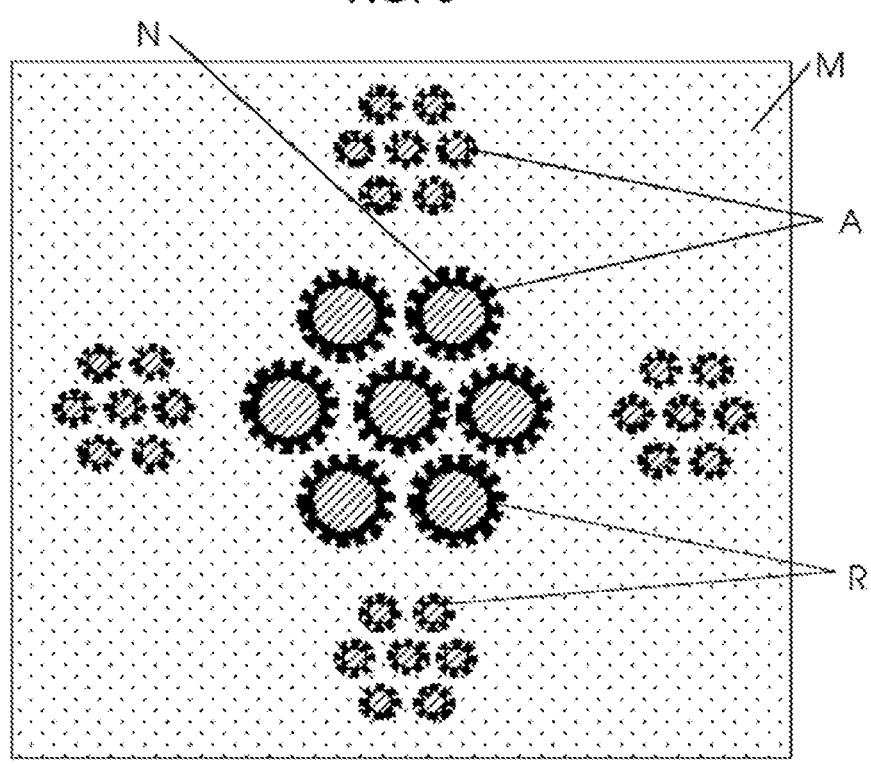

FIGS. 8 and 9 show some chromatic effects (outer rings) perceived by the subject during the subjective refraction procedure, using the visual stimulus of FIG. 7. In these two figures, the colour magenta M (the colour of the background) has been represented with dots, whereas the colour black N (the colour of the circles) has been represented by means of stripes. The chromatic effects have been represented in black, with the black ring R surrounding each circle being the red chromatic effect and the black "teeth" A projecting from the ring being the blue chromatic effect.

In the image of FIG. 8, the subject is further away from the optimal subjective refraction and perceives a greater fluctuation and chromatic effect. In FIG. 9, after performing the adjustment of step iv, the subject is closer to the best subjective refraction and perceives a lower fluctuation and less chromatic effects, and the image perceived by the subject is closer to the real image of the visual stimulus shown in FIG. 7.

Although a red-blue bichromatic stimulus has been used in the described example, other bichromatic combinations such as, for example, red-green and green-blue, can also be used. Although the shown stimulus is formed by a set of circles or dots, it can likewise comprise letters, numbers, other polygonal shapes, or drawings, or combinations of these elements.

The apparatus 100 may comprise in particular two opto-adjustable lenses 11, one for each eye 10 of the patient. In such case, the apparatus 100 also comprises two optical projector systems.

The periodic defocusing optical power wave 200 may have a square wave profile (such as the one shown in FIG. 3) or a sine wave profile (such as the one shown in FIG. 6). The mean value of the periodic optical power wave may vary based on patient responses following different methods: an adjustment method, a staircase method, a forced-choice method forcing a choice between several alternatives, an adaptive method, or a constant stimulus method.

Although the detailed description focuses on application in a subjective refraction procedure, it is understood that one skilled in the art could use the described apparatus, system, and method in other applications.

For example, the proposed system can be used for visual training. Furthermore, taking into account that the proposed apparatus, system, and method are not affected by the accommodation of the subject, it can also be used for training conscious accommodation and thereby delaying the effects of presbyopia.

It can also be used for adjusting the focus of an opto-adjustable lens at a distance X by placing a visual stimulus in said position X and adjusting the optical power wave of the opto-adjustable lens such that the chromatic and fluctuation effects are minimised or made to be non-existent.

It could also be used to alter the graphical effects perceived by a user when he or she looks at a screen through the apparatus, allowing the chromatic effects and fluctuations perceived by the subject to be adjusted; this alteration can be used, for example, for video games in which the subject obtains points or overcomes certain levels when the chromatic effects and fluctuations disappear.

In view of this description and figures, one skilled in the art may understand that the disclosure has been described according to some preferred embodiments thereof, but that multiple variations can be introduced in said preferred embodiments without departing from the object of the disclosure as claimed.

In this text, the term "comprises" and its derivations (such as "comprising", etc.) must not be understood in an excluding manner. In other words, these terms must not be interpreted as excluding the possibility that what is described and defined may include more elements, steps, etc.

The invention claimed is:

1. An apparatus for performing optometric measurements, the apparatus comprising:
   an opto-adjustable lens having an adjustable optical power, said opto-adjustable lens being controlled by a periodic signal configured for producing a periodic optical power wave over time;
   an actuator for adjusting the mean value of the periodic optical power wave by adjusting the geometry of the opto-adjustable lens;
   wherein the apparatus further comprises
   an optical projector system for projecting a plane of the opto-adjustable lens onto a plane external to the apparatus;
   wherein the periodic signal has an amplitude such that it produces an amplitude of the periodic optical power wave corresponding to a chromatic difference of focus between a first wavelength and a second wavelength of visible light passing through the opto-adjustable lens;
   wherein the plane external to the apparatus is a plane of a pupil of the eye of a subject, and the chromatic difference of focus is that which is produced in the eye of the subject when the subject looks through the apparatus.

2. The apparatus of claim 1, which further comprises means for adjusting the amplitude of the periodic optical power wave to different combinations of values of the first visible wavelength and of the second visible wavelength.

3. The apparatus of claim 1, wherein the periodic optical power wave has a frequency lower than a flicker fusion threshold.

4. The apparatus of claim 3, wherein the frequency is between 10 and 40 Hz.

5. The apparatus of claim 4, wherein the frequency is 15 Hz.

6. The apparatus of claim 1, wherein the amplitude of the periodic optical power wave is between 0.25 dioptres and 3 dioptres.

7. The apparatus according of claim 1, wherein the amplitude of the periodic optical power wave is 0.75 dioptres.

8. The apparatus of claim 1, wherein that the apparatus further comprises a variable iris diaphragm.

9. A system for performing optometric measurements on an eye of a subject, the system comprising:
   a visual stimulus with elements in at least two different colours; and
   an apparatus according to claim 1.

10. The system of claim 9, wherein one of the at least two different colours of the visual stimulus is a combination of the first wavelength and the second wavelength.

11. The system of claim 9, wherein the first and second wavelengths are blue and red, and one of the at least two colours of the elements of the visual stimulus is magenta.

12. The system of claim 11, wherein one of the at least two colours of the elements of the stimulus is black.

13. The apparatus of claim 1, wherein the amplitude of the periodic optical power wave is between 0.75 dioptres and 1.5 dioptres.

14. The apparatus of claim 1, wherein the amplitude of the periodic optical power wave is between 0.25 dioptres and 0.75 dioptres.

15. A method for adjusting the optical power of an opto-adjustable lens, the method comprising the following steps:
   making a subject look at a visual stimulus through an opto-adjustable lens the optical power of which is adjustable,
   projecting the plane of the opto-adjustable lens onto a pupil of an eye of the subject;
   controlling the opto-adjustable lens by means of a periodic signal and producing a periodic optical power wave the amplitude of which corresponds to a chromatic difference of focus produced in the eye of the subject between a first wavelength and a second wavelength of visible light, the visual stimulus comprising elements in at least two different colours, one of the at least two colours being a combination of the first wavelength and the second wavelength; and
   adjusting the mean value of the periodic optical power wave to reduce or eliminate chromatic effects and fluctuation of the visual stimulus perceived by the subject.

16. The method of claim 15, the method being carried out with an apparatus for performing optometric measurements, the apparatus comprising:
   an opto-adjustable lens having adjustable optical power, the optical power of which is adjustable, said opto-adjustable lens being controlled by a periodic signal configured for producing a periodic optical power wave over time;
   means an actuator for adjusting the mean value of the periodic optical power wave by adjusting the geometry of the opto-adjustable lens;
   wherein the apparatus further comprises
   an optical projector system for projecting a plane of the opto-adjustable lens onto a plane external to the apparatus;
   and wherein
   the periodic signal having an amplitude which has an amplitude such that it produces an amplitude of the periodic optical power wave corresponding to a chromatic difference of focus between a first wavelength and a second wavelength of visible light passing through which passes the opto-adjustable lens.

17. The method of claim 15, wherein the chromatic effects perceived by the subject in the visual stimulus include a colour change to blue or red.

18. The method of claim 16, wherein the chromatic effects perceived by the subject in the visual stimulus include a colour change to blue or red.

* * * * *